United States Patent [19]
Dolbier, Jr. et al.

[11] Patent Number: 5,841,005
[45] Date of Patent: Nov. 24, 1998

[54] PARYLENE AF4 SYNTHESIS

[76] Inventors: William R. Dolbier, Jr., 8205 S.W. 39th Pl., Alachua, Fla. 32608; Jian-Xin Duan, 1404 S.W. 10th Ter., Apartment 23; Alex J. Roche, 716 S.W. 16th Ave, both of Alachua, Fla. 32601

[21] Appl. No.: 818,584

[22] Filed: Mar. 14, 1997

[51] Int. Cl.⁶ .................................................. C07C 22/08
[52] U.S. Cl. ........................ 570/144; 570/143; 570/148
[58] Field of Search .................................. 570/143, 144, 570/148

[56] References Cited

U.S. PATENT DOCUMENTS

| | | |
|---|---|---|
| 3,211,128 | 10/1965 | Potter et al. . |
| 3,246,627 | 4/1966 | Loeb et al. . |
| 3,268,599 | 8/1966 | Chow . |
| 3,274,267 | 9/1966 | Chow . |
| 3,297,591 | 1/1967 | Chow . |
| 3,301,707 | 1/1967 | Loeb et al. . |
| 3,472,795 | 10/1969 | Tittmann et al. . |
| 3,554,512 | 1/1971 | Elliott . |
| 3,570,449 | 3/1971 | Blecherman . |
| 3,573,968 | 4/1971 | Loeb . |
| 3,600,216 | 8/1971 | Stewart . |
| 3,667,424 | 6/1972 | Cornelius et al. . |
| 3,670,693 | 6/1972 | Rorick et al. . |
| 3,747,558 | 7/1973 | Harel . |
| 3,749,601 | 7/1973 | Tittle . |
| 4,110,392 | 8/1978 | Yamazaki . |
| 4,184,188 | 1/1980 | Briglia . |
| 4,261,762 | 4/1981 | King . |
| 4,323,031 | 4/1982 | Kaplan . |
| 4,362,125 | 12/1982 | Schadler . |
| 4,401,052 | 8/1983 | Baron et al. . |
| 4,468,283 | 8/1984 | Ahmed . |
| 4,495,889 | 1/1985 | Riley . |
| 4,508,055 | 4/1985 | Elton et al. . |
| 4,518,623 | 5/1985 | Riley . |
| 4,577,465 | 3/1986 | Olsen et al. . |
| 4,596,208 | 6/1986 | Wolfson et al. . |
| 4,613,306 | 9/1986 | Bauer et al. . |
| 4,619,844 | 10/1986 | Pierce et al. . |
| 4,683,143 | 7/1987 | Riley . |
| 4,734,533 | 3/1988 | Ungarelli et al. . |
| 4,761,269 | 8/1988 | Conger et al. . |
| 4,783,561 | 11/1988 | Pregaglia et al. . |
| 4,795,838 | 1/1989 | Bornengo et al. . |
| 4,816,608 | 3/1989 | Bornengo et al. . |
| 4,846,998 | 7/1989 | Pohl et al. . |
| 4,853,488 | 8/1989 | Ungarelli et al. . |
| 4,877,433 | 10/1989 | Oshitari . |
| 4,883,020 | 11/1989 | Kasai et al. . |
| 4,886,923 | 12/1989 | Ungarelli et al. . |
| 4,902,572 | 2/1990 | Horne et al. . |
| 4,903,754 | 2/1990 | Hirscher et al. . |
| 4,945,856 | 8/1990 | Stewart . |
| 4,957,781 | 9/1990 | Kanegae et al. . |
| 5,002,011 | 3/1991 | Ohmine et al. . |
| 5,007,372 | 4/1991 | Hattori . |
| 5,015,503 | 5/1991 | Varrin, Jr. et al. . |
| 5,078,091 | 1/1992 | Stewart . |
| 5,078,851 | 1/1992 | Nishihata et al. . |
| 5,079,045 | 1/1992 | Luhmann et al. . |
| 5,088,444 | 2/1992 | Ohmine et al. . |
| 5,091,207 | 2/1992 | Tanaka . |
| 5,112,642 | 5/1992 | Wajid . |
| 5,121,707 | 6/1992 | Kanoo . |
| 5,123,375 | 6/1992 | Hansen . |
| 5,129,360 | 7/1992 | Ahern et al. . |
| 5,151,133 | 9/1992 | Ohmine et al. . |
| 5,167,717 | 12/1992 | Boitnott . |
| 5,186,120 | 2/1993 | Ohnishi et al. . |
| 5,210,341 | 5/1993 | Dolbier ................................... 570/144 |
| 5,217,755 | 6/1993 | Thebault et al. . |
| 5,221,403 | 6/1993 | Nozawa et al. . |
| 5,228,501 | 7/1993 | Tepman et al. . |
| 5,248,370 | 9/1993 | Tsui et al. . |

(List continued on next page.)

FOREIGN PATENT DOCUMENTS

| | | |
|---|---|---|
| 0 102 417 A1 | 3/1984 | European Pat. Off. . |
| 0 434 227 A1 | 6/1991 | European Pat. Off. . |
| 0 679 373 A2 | 11/1995 | European Pat. Off. . |
| 650947 | 3/1951 | United Kingdom . |
| WO 82/03069 | 9/1982 | WIPO . |

OTHER PUBLICATIONS

CA:124:77935 Isolation & Structure of Col 4A6 Gene Encoding the Human Alpha 6(IV) chain, Oohashi J. Biochem 270 (75)26863–7.

Chow, S.W., "Poly ($\alpha,\alpha,\alpha',\alpha'$-tetrafluoro–p–xylylene)", *Journal of Applied Polymer Science*, vol. 13, pp. 2325–2332, 1969.

Ho, T.L., et al., Communications, p. 170–171, Mar. 1977.

Olah, G.A., et al.,. Communications, pp. 607–609, Sep. 1976.

Eisch, J.J., et al., Tetrahedron Letters, vol. 24, No. 20, pp. 2043–2046, 1983.

Cooper, T.A., J. Am. Chem. Soc., 95, pp. 4158–4162, Jun. 27, 1973.

Chow, S.W., J. Org. Chem., vol. 35, pp. 20–22, Jan. 14, 1969.

Pons, J–M., Tetrahedron, vol. 44, pp. 4295–4312, 1988.

S.W. Chow. L.A. Pilato, and W.L. Wheelwright, The Synthesis of 1,1,2,2,9,9,10,10–Octafluoro[2.2]paracyclophane, Journal of Organic Chemistry 32, 20 (1970).

William R. Dolbier, Jr., et al., A New Synthesis of Octafluoro[2.2]paracyclophane, Journal of Organic Chemistry 58, 1827 (1993).

W.R. Hasek, et al., The Chemistry of Sulfur Tetrafluoride, II. The Fluorination of Organic Carbonyl Compounds, Journal of the Am. Chem. Soc. 82, 543 (1960).

*Primary Examiner*—Alan L. Rotman
*Assistant Examiner*—Jean F. Vollano
*Attorney, Agent, or Firm*—Mintz, Levin, Cohn, Ferris, Glovsky and Popeo, P.C.

[57] ABSTRACT

Methods of making parylene AF4 using novel that result in reduced cost. Low dilution technology may used to provide parylene AF4 in substantially improved yields. The relative amount of transition metal catalyst can be decreased. The amount of undesired byproduct is also reduced.

42 Claims, No Drawings

U.S. PATENT DOCUMENTS

| | | |
|---|---|---|
| 5,248,380 | 9/1993 | Tanaka . |
| 5,250,092 | 10/1993 | Nakano . |
| 5,250,323 | 10/1993 | Miyazaki . |
| 5,254,171 | 10/1993 | Hayakawa et al. . |
| 5,261,963 | 11/1993 | Basta et al. . |
| 5,262,194 | 11/1993 | Bisher, Jr. et al. . |
| 5,264,039 | 11/1993 | Gobush et al. . |
| 5,266,118 | 11/1993 | Mitra . |
| 5,268,033 | 12/1993 | Stewart . |
| 5,268,202 | 12/1993 | You et al. . |
| 5,270,266 | 12/1993 | Hirano et al. . |
| 5,292,554 | 3/1994 | Sinha et al. . |
| 5,302,767 | 4/1994 | Galley et al. . |
| 5,324,540 | 6/1994 | Terada . |
| 5,344,492 | 9/1994 | Sato et al. . |
| 5,350,453 | 9/1994 | Schlosser . |
| 5,401,316 | 3/1995 | Shiraishi et al. . |
| 5,439,525 | 8/1995 | Peichl et al. . |
| 5,447,799 | 9/1995 | Loh et al. . |
| 5,458,687 | 10/1995 | Schichida et al. . |
| 5,534,068 | 7/1996 | Beach et al. . |
| 5,536,892 | 7/1996 | Dolbier ............ 570/144 |

PARYLENE AF4 SYNTHESIS

BACKGROUND

1. Field of the Invention

The present invention relates generally to parylene AF4 synthesis, and more specifically to parylene AF4 synthesis that involves novel reducing agents.

2. Discussion of the Related Art

Parylene is a generic term often used to describe a class of poly-p-xylenes which may be derived from a dimer of the structure:

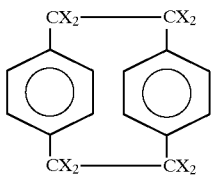

wherein X is typically a hydrogen atom or a halogen atom.

The most commonly used forms of these dimers include:

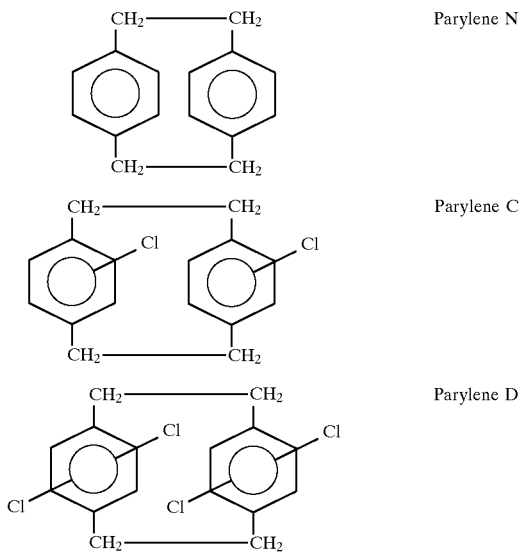

Octafluoro-[2,2]paracyclophane (hereinafter "AF4") is a fluorine substituted version of the above dimer having the structure:

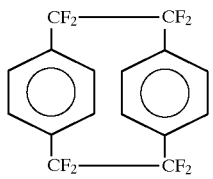

Parylene materials derived from AF4 are capable of providing thin films and conforming to substrates of varied geometric shapes, allowing for their use as conformal coatings. Furthermore, these coatings have a relatively high melting temperature (about 540° C.) and a comparatively low dielectric constant (about 2.3). These characteristics make parylene layers formed from AF4 well suited for many different applications, such as, for example, the electronics, automotive and medical industries.

Despite the desire to produce large quantitites of AF4, known methods of making AF4 can be too expensive to be used on a commercial scale. In part, the high cost is due to the relatively low yields provided by these processes. In addition, the materials used in these synthetic schemes can be comparatively expensive. Furthermore, known methods of making AF4 typically use high dilution technology which can result in comparatively large costs associated with solvent purchase, storage, handling and disposal. Therefore, it is desirable within the art to provide a relatively inexpensive method of synthesizing AF4. In particular, it would be advantageous to provide a method of making AF4 that results in increased product yield, reduced reagent cost and/or reduced solvent use.

SUMMARY

In one illustrative embodiment, the present invention provides a method of making AF4. The method comprising the step of: mixing a dihalo compound with a reducing agent to form a reaction mixture, the dihalo compound comprising at least about $1\times10^{-3}$ weight percent of the reaction mixture; and reacting the reaction mixture to form product materials including the AF4.

In another illustrative embodiment, the present invention provides a method of making AF4. The method comprises the steps of: mixing a dihalo compound and a reducing agent to form a reaction mixture, the reducing agent comprising at least about $1\times10^{-3}$ weight percent of the reaction mixture; and reacting the reaction mixture to form product materials including the AF4.

In a further illustrative embodiment, the present invention provides a method of making AF4. The method comprises the steps of: mixing a dihalo compound with a reducing agent to form a reaction mixture, the reducing agent having an electrochemical potential of from about +0.45 volts to about +2.5 volts relative to a standard hydrogen potential; and allowing the reaction mixture to react to form product materials including the AF4.

DETAILED DESCRIPTION

The present invention relates to AF4 synthesis by the chemical reaction of a 1,4-bis(halodifluoromethyl) benzene (hereinafter a "dihalo" compound) with a reducing agent either alone or in the presence of a transition metal catalyst and a solvent.

A "dihalo" compound herein refers to 1,4-bis (chlorodifluoromethyl) benzene (hereinafter "dichloro"), 1,4-bis(bromodifluoromethyl) benzene (hereinafter "dibromo") or 1,4-bis(iododifluoromethyl) benzene (hereinafter "diiodo"). While AF4 synthesis can be performed at lower temperature with diiodo (about room temperature) or dibromo (about 80° C.) than dichloro (from about 90° C. to about 140° C.), dichloro is preferred because it is less expensive than diiodo or dibromo.

The term "reducing agent" as used herein refers to any compound that is capable of removing the chlorine atoms from dichloride, removing the bromine atoms from dibromide or removing the iodine atoms from the diiodide. Unexpectedly, it has been found that the use of certain metals as reducing agents results in relatively high yields of AF4. In particular, metals having an electrochemical potential of from about +0.45 volts to about +2.5 volts relative to the standard hydrogen gas electrode are effective in producing these relatively high yields. Preferably, the reducing agent is zinc, magnesium, aluminum, copper, iron, manganese, cadmium, mercury, nickel or tetrakis-(dimethylamino)ethylene, more preferably the reducing agent is zinc or magnesium, and most preferably the reducing agent is zinc. Typically, the reducing agent is in the form of a powder. Since zinc powder is comparatively inexpensive, the use of this material as the reducing agent offers the additional advantage of reduced cost in AF4 synthesis.

Transition metal catalysts appropriate for use in the present invention may be nickel, palladium, copper, rhodium, ruthenium, cobalt, iron or chromium catalysts. Such catalysts include, for example, $NiCl_2$, tetrakis (triphenylphosphine)palladium[0] and $RhCl_3$. While certain transition metal catalysts have been disclosed herein, it is to be understood that this list is not exclusive. Transition metal catalysts for use in AF4 synethsis are limited only in that they should be capable of stabilizing the reaction intermediate to allow coupling of this intermediate in AF4 formation, as discussed below.

Solvents appropriate for use in the present invention should be capable of facilitating the AF4 synthesis reaction. An illustrative and nonlimiting list of such solvents includes acetic anhydride, tetrahydrofuran (hereinafter "THF"), dimethylsulfoxide (hereinafter "DMSO"), dimethylformamide (hereinafter "DMF"), n-methyl pyrrolidone (hereinafter "NMP"), 1,3-dimethyl-2-imidazolidinone (hereinafter "DMEU"), diethyl ether, 1,3-dioxane, 2-methoxyethyl ether (hereinafter "diglyme"), hexamethylphosphotriamide (hereinafter "HMPA"), N,N-dimethylacetamide (hereinafter "DMA"), and N-methylmorpholine.

In certain embodiments, AF4 synthesis includes the use of from about 1.5 to about 2.5 moles of reducing agent per mole of dihalo compound. In addition, from about 0.01 mole percent to about 0.1 mole percent of transition metal catalyst is typically used per mole of dihalo compound. In some embodiments, AF4 synthesis can be performed with heating at a temperature below refluxing combined with vigorous stirring.

Despite the reduced cost that would result from increasing the yield of AF4, known methods of making AF4 have resulted in yields of AF4 no greater than about 40 molar percent relative to the amount of dihalo compound used in the reaction mixture. Surprisingly, however, the present invention provides a method of making AF4 that results in a relatively high yield of AF4. According to the present invention, the yield of AF4 is preferably at least about 20 molar percent relative to the amount of AF4 used in the reaction mixture, more preferably at least about 40 molar percent and most preferably at leat about 80 molar percent. These comparatively high yields of AF4 decrease the overall cost of AF4 production and result in an approach to making AF4 that is commercially viable.

Known methods of making AF4 have involved reaction mechanisms in which a diradical intermediate is formed. This intermediate has two principle reaction pathways. The first pathway is for cyclization to occur to form AF4. This reaction is unimolecular and, therefore, independent of the concentration of the intermediate in the reaction mixture. The second principle reaction pathway includes the reaction between two intermediates to form a linear byproduct which can undergo further reactions, ulimately resulting in a polymer byproduct. This pathway involves bimolecular reactions which depend upon the concentration of the intermediate in the reaction mixture. Thus, to optimize the yield of AF4 relative to the polymer byproduct, the conventional wisdom has been to use high dilution technology when synthesizing AF4. "High dilution technology" us used herein refers to a method of AF4 synthesis in which the concentration of the dihalo compound and/or the reducing agent is controlled such that, at any time during the reaction, the dihalo compound and/or the reducing agent is at most about $5\times10^{-6}$ weight percent of the overall reaction mixture.

Surprisingly, the present invention provides a method of AF4 synthesis that can be performed under conditions of low dilution technology. "Low dilution technology" herein denotes an AF4 synthesis process in which, at some time during the reaction, the dihalo compound and/or the reducing agent is at least about $1\times10^{-3}$ weight percent of the overall reaction mixture. Preferably, AF4 synthesis occurs under conditions in which, at any time during the reaction, the dihalo compound and/or the reducing agent is at least about 5 weight percent of the reaction mixture, more preferably at least about 9 weight percent and most preferably at least about 15 weight percent. Without wishing to be bound by any theoretical explanations, it is believed that low dilution technology can be used in the present invention because AF4 synthesis occurs without the forming the diradical intermediate. Instead, due to the surprisingly low yield of linear product, it is believed that the reaction proceeds via electron transfer in which direct coupling of the reaction intermediate occurs, thereby allowing the use of low dilution technology.

The use of low dilution technology for AF4 synthesis provides the advantage of lower costs associated with purchasing, storing, handling and disposing of solvents. Furthermore, low dilution technology allows for an easier scale up of the AF4 synthesis process to a commercial level because, for a given amount of AF4 produced, the decreased amount of solvent used results in a smaller volume of reaction mixture.

Prior methods of synthesizing AF4 have resulted in a yield of linear byproduct of at least about 40 molar percent relative to the total amount of material formed by the reaction. "Linear byproduct" herein denotes a linear structure resulting from the chemical reaction of more than one molecule of dihalo compound. However, in certain embodiments, the present invention provides a process for preparing AF4 in which substantially no linear byproduct is produced. Preferably, the yield of linear byproduct is less than about 30 molar percent relative to the total amount of material formed by the reaction, more preferably less than about 20 molar percent and most preferably less than about 10 molar percent.

Previously known AF4 synthesis methods produce at least about 18 percent reduction byproduct relative to the total amount of material formed by the reaction. The term "reduction byproduct" as used herein refers to a linear structure of one or more monomer units in which one or more of the chlorine, bromine or iodine atoms has been replaced by a hydrogen atom. In some embodiments, however, the process of the present invention can produce AF4 while producing substantially no reduction byproduct. According to the present invention, AF4 synthesis preferably produces less than about 10 molar percent reduction byproduct relative to the total amount of material formed by the reaction, more preferably less than about 5 molar percent reduction byproduct and most preferably less than about 1 molar percent reduction byproduct.

Whereas known methods did not involve the use of transition metal catalysts, the method of making AF4 in accordance with the present invention can involve the use of a transition metal catalyst, typically present in relatively small amounts of the overall reaction mixture. Preferably, the transition metal catalyst comprises less than about 0.1 molar percent of the reaction mixture, more preferably less than about 0.01 molar percent of the reaction mixture and most preferably substantially none of the reaction mixture.

The following examples are provided for illustrative purposes only and are not intended to limit the scope of the present invention.

EXAMPLE I

Dichloride was made as follows. About 500 grams of α,α,α',α'-tetrafluoro-p-xylene (hereinafter "TFPX"), prepared by the method disclosed in commonly owned and co-pending U.S. patent application Ser. No. 08/735,726 or by other methods known to those skilled in the art, is dissolved in about 750 mL of carbon tetrachloride (available from Aldrich Chemical, located in Milwaukee, Wis.). Chlorine gas was bubbled through this solution for about 36 hours while the solution is exposed to ultraviolet radiation emitted by a mercury lamp. After about 36 hours, about 2 equivalents of chlorine were reacted. The yield of dichloride was greater than about 90 mole percent.

EXAMPLE II

Dichloride was prepared using a method similar to the method of Example I but without the use of a solvent. The step of bubbling the chlorine gas with ultraviolet radiation exposure was carried out for about 24 hours or less.

EXAMPLE III

Dibromo was prepared according to the method disclosed in *Journal of the American Chemical Society* 82, 543 (1960) by reacting terephthaldehyde with sulfur tetrafluoride at temperatures of about 150° C. to provide α,α,α',α'-tetrafluoro-p-xylylene. About 0.15 moles of the α,α,α',α'-tetrafluoro-p-xylylene was admixed with about 0.33 moles of N-bromosuccinimide and about 320 parts of carbon tetrachloride. The mixture was irradiated with a mercury lamp while being maintained at the reflux temperature of the carbon tetrachloride. The precipitated succinimide was removed by filtration, and the filtrate was distilled to yield about 0.12 moles of dibromo having a boiling point of about from about 102° C. to about 107° C. at a pressure of about 25 mm Hg.

EXAMPLE IV

About 7.0 grams of zinc powder (available from Fisher Scientific, located in Atlanta, Ga.), about 0.14 grams of $NiCl_2$ (available from Aldrich) and about 80 milliliters of acetic anhydride (available from Aldrich) were placed in a 150 milliliter flask. This mixture was stirred for about 15 minutes under a nitrogen atmosphere at room temperature and subsequently brought to mild refluxing at about 140° C. About 18 grams of dichloro (available from Aldrich) in 20 milliliters of acetic anhydride was added dropwise to the refluxing mixture over a period of about two hours. The resulting mixture was then stirred with refluxing for about 30 minutes after which an internal standard of trifluoromethylbenzene was added. $^{19}F$ NMR demonstrated that the yield of AF4 was about 40 mole percent.

An equal amount of chloroform (available from Aldrich) was added to the AF4. This mixture was stirred for about one hour at a temperature of about 60° C. The mixture was then filtered, and the chloroform was evaporated from the filtrate. Water was added to the filtrate, precipitating the AF4 which was subsequently filtered. This filtrate was then sublimed at a temperature of about 150° C. and a pressure of about 10 mm Hg and recrystallized from pentane to isolate about 3.2 grams (30 mole percent) of AF4 which was characterized by $^{19}F$ NMR as well as mass spectroscopy.

EXAMPLE V

A three-necked 100 milliliter round bottomed flask was fitted with a pressure equalizing dropping funnel containing about 4.1 grams of dichloro, a reflux condenser attached to a nitrogen bubbler and a large magnetic stirrer. The flask was charged with about 30 milliliters of DMSO (available from Aldrich), about 1.7 grams of zinc powder and about 0.011 grams of tetrakis (tripehenlyphosphine) palladium [0] (available from Aldrich) under dry nitrogen. The system was flushed with nitrogen for about 30 minutes and warmed to about 130° C. The nitrogen flow was then stopped and the dichloride was added dropwise to the vigorously stirred solution over about two hours. The reaction temperature was maintained between about 125° C. and about 140° C. for a period of about 18 hours.

After cooling to room temperature, about 100 milliliters of chloroform was added to the stirred solution, and, after about 30 minutes, the green reaction mixture was filtered, producing a green filtered solid and a pale yellow filtrate. A $^{19}F$ NMR spectrum of the filtrate revealed the presence of only two major components, identified as unreacted dichloride (about 35 mole percent) and AF4 (about 47 mole percent), as determined by integration against an internal standard of trifluoromethylbenzene. Based on conversion of the starting material, the yield of AF4 was calculated to be about 73 mole percent.

The product was isolated from the reaction mixture by removing the chloroform be evaporation and adding about 200 milliliters of water to the remaining DMSO solution. This procedure resulted in the precipitation of a pale yellow solid which was recrystallized.

EXAMPLE VI

The AF4 synthesis process of Example V was repeated using about 3.5 grams of dichloride in about 50 mL of DMSO. The solution was heated overnight at about 140° C. About 3.6 equivalents of zinc powder and about 0.05 mole percent of $NiCl_2$ were used. The yield of AF4 was about 47 mole percent.

EXAMPLE VII

The AF4 synthesis process of Example V was repeated using about 4.5 grams of dichloride in about 50 mL of DMF (available from Aldrich). The solution was heated overnight at about 140° C. About 1.6 equivalents of zinc powder and about 0.05 mole percent of catalytic $Pd(Ph_3P)_4$ were used. The product led to recovery of about 8 mole percent dichloride and about 48 mole percent AF4. Based on the conversion of dichloride, the yield of AF4 was about 52 mole percent.

EXAMPLE VIII

The AF4 synthesis process of Example V was repeated using about 3 grams of dichloride in about 7.7 mL of DMF. The solution was heated for about 24 hours at about 110° C. About 2 equivalents of zinc powder and about 0.05 mole percent of catalytic $RhCl_3$ were used. Based on the conversion of dichloride, the yield of AF4 was about 63 mole percent.

EXAMPLE IX

The AF4 synthesis process of Example V was repeated using about 50 grams of dichloride in about 500 mL of DMF.

The solution was heated for about 24 hours at from about 90° C. to about 110° C. About 2 equivalents of zinc powder and no catalyst were used. The yield of AF4 was about 40 mole percent.

EXAMPLE X

The AF4 synthesis process of Example V was repeated using about 6.2 grams of dibromide in about 50 mL of DMSO. The solution was heated for about 24 hours at 80° C. About 3.1 equivalents of zinc powder and about 0.05 mole percent of catalytic Pd(Ph$_3$P)$_4$ were used. The yield of AF4 was about 23 mole percent.

EXAMPLE XI

About 0.15 grams of magnesium powder (available from Aldrich), about 0.001 grams of RhCl3 and about 16 milliliters of THF (available from Aldrich) were placed in a 150 milliliter flask. This mixture was stirred for about 10 minutes under a nitrogen atmosphere at room temperature and subsequently brought to mild refluxing at about 70° C. About 3 grams of dichloro in 20 milliliters of THF was added dropwise to the refluxing mixture over a period of about two hours. The resulting mixture was then stirred with refluxing for about 22 hours after which an internal standard of trifluoromethylbenzene was added. $^{19}$F NMR showed a conversion of dichloride of about 10 mole percent, indicating that the yield of AF4 was about 73 mole percent.

EXAMPLE XII

The AF4 synthesis process of Example V was repeated using about 60 grams of dichloride in about 600 mL of DMA. The solution was heated for about 48 hours at about 85° C. About 2 equivalents of zinc powder and no catalyst were used. The yield of AF4 was about 70 mole percent, and the conversion was about 100%.

Certain illustrative and nonlimiting examples of AF4 synthesis are listed in Table I.

TABLE I

| | dihalo | dihalo mass (grams) | reducing agent (% purity) | equivs of reducing agent | metal catalyst | equivs of metal catalyst | solvent and volume (mL) | temp (°C.) | time (hours) | convert (%) | Yield AF4 (%) |
|---|---|---|---|---|---|---|---|---|---|---|---|
| 1 | dichloro | 18 | Zn (97) | 1.5 | NiCl2 | 0.05 | Ac2O 100 | 140 | 24 | 100 | 40 |
| 2 | dichloro | 11 | Zn (97) | 1.6 | RhCl3 | 0.05 | Ac2O 60 | 140 | 12 | 100 | 30 |
| 3 | dichloro | 4.5 | Zn (97) | 1.6 | Pd(Ph3P)4 | 0.05 | DMF 30 | 140 | 12 | 48 | 52 |
| 4 | dichloro | 4.5 | Zn (97) | 3 | Pd(Ph3P)4 | 0.05 | DMSO 10 | 140 | 12 | 100 | 13 |
| 5 | dichloro | 3 | Zn (97) | 1.6 | RhCl3 | 0.05 | DMF 7.7 | 110 | 12 | 20 | 63 |
| 6 | dibromo | 6.2 | Zn (99) | 3.1 | Pd(Ph3P)4 | 0.05 | DMSO 50 | 80 | 12 | 100 | 23 |
| 7 | dichloro | 2.6 | Zn (97) | 4.0 | None | | DMSO 20 | 100 | | 100 | 24 |
| 8 | dichloro | 4.1 | Zn (99) | 3.2 | Pd(Ph3P)4 | 0.05 | DMSO 50 | 140 | 12 | 100 | 24 |
| 9 | dichloro | 5.3 | Zn (97) | 3.5 | CuBr | 0.05 | DMSO 50 | 140 | 12 | 100 | 4 |
| 10 | dichloro | 50 | Zn (99) | 2 | None | | DMF 500 | 100 | | 100 | 40 |
| 11 | dichloro | 5 | Zn (99) | | None | | DMF 50 | 85 | 30 | 88 | 14 |
| 12 | dichloro | 5 | Zn (99) | 2 | None | | DMF 50 | 90 | 20 | 62 | 39 |
| 13 | dichloro | 6.5 | Zn (99) | 2 | None | | DMA 60 | 100 | 48 | 100 | 0 |
| 14 | dichloro | 6.1 | Zn (99) | 2 | None | | NMP 60 | 100 | 24 | 100 | 61 |
| 15 | dibromo | 2.1 | Zn (99) | 2 | None | | DMA 20 | 50 | 12 | 100 | 28 |
| 16 | dichloro | 60 | Zn (99) | 2 | None | | DMA 600 | 85 | 48 | 100 | 70 |
| 17 | dichloro | 13.8 | Zn (97) | 2 | None | | DMA 138 | 100 | 72 | 70 | 63 |
| 18 | dichloro | 6.5 | Zn (99) | 2 | None | | DMA 60 | 100 | 70 | 100 | 42 |
| 19 | dichloro | 6.5 | Al (99.95) | 1.3 | None | | DMA 60 | room temp. | 18 | 0 | 0 |
| 20 | dichloro | 6.5 | Al (99.95) | 1.3 | None | | DMA 60 | 60–70 | 24 | 0 | 0 |
| 21 | dichloro | 6.5 | Al (99.95) | 5 | None | | DMA 60 | 100 | 24 | 0 | 0 |
| 22 | dichloro | 5 | Mg (99+) | 2 | None | | DMA 50 | 0–room temp | 20 | 100 | 0 |
| 23 | dichloro | 10 | Mg (99+) | 2 | None | | DMA 100 | room temp–50 | 1 | low | 0 |
| 24 | dichloro | 10 | Mg (99+) | 2 | None | | DMA 100 | 50 | 20 | low | 0 |

TABLE I-continued

| | dihalo | dihalo mass (grams) | reducing agent (% purity) | equivs of reducing agent | metal catalyst | equivs of metal catalyst | solvent and volume (mL) | temp (°C.) | time (hours) | convert (%) | Yield AF4 (%) |
|---|---|---|---|---|---|---|---|---|---|---|---|
| 25 | dichloro | 5.2 | Fe (99+) | 2 | None | | DMA 60 | 100 | 20 | low | 0 |
| 26 | dichloro | 6 | Zn (97) | 2 | None | | DMA 60 | 90 | 49 | 100 | 64 |
| 27 | dichloro | 5.3 | Zn (99) | 2 | AgOAc | 2 | DMA 60 | 40–60 | 60 | 95 | 19 |
| 28 | dichloro | 5.3 | Zn (99) | 2 | None | | DMA/THF 60(4:1) | 100 | 48 | 87 | 11 |
| 29 | dichloro | 10 | Zn (99) | 1.3 | None | | DMA 100 | 100 | 48 | 81 | 76 |
| 30 | dichloro | 5.2 | Zn (99) | 2 | AgOAc | 0.3 | DMA 60 | room temp | 48 | 0 | 0 |
| 31 | dichloro | 6.5 | Zn (99) | 2 | None | | DMA 60 | 90–100 | 24 | 95 | 55 |
| 32 | dichloro | 5.2 | Zn (99) | 2 | AgOAc | 0.3 | DMA 60 | 40–60 | 24 | 0 | |
| 33 | dichloro | 5.2 | Zn (99) | 2 | AgOAc | 0.3 | DMA 60 | 90–100 | 48 | 87 | 40 |
| 34 | dichloro | 30 | Zn (99) | 1.5 | None | | DMA 300 | 85–90 | 48 | 88 | 63.7 |
| 35 | dichloro | 6.2 | Zn (99) | 2.1 | None | | DMA 60 | 100–110 | 21 | 90 | 51 |
| 36 | dichloro | 6.3 | Zn (99) | 2 | None | | DMA 60 | 100–110 | 20 | 94 | 38 |
| 37 | dichloro | 5.8 | Zn (99) | 2.2 | None | | DMA 60 | 100–110 | 20 | 100 | 39 |
| 38 | dichloro | 6.4 | Zn-act | 2.1 | None | | DMA 60 | 100–110 | 26 | 94 | 37 |
| 39 | dichloro | 6 | TDAE | 2 | None | | DMA 60 | 100–110 | 24 | 90 | 5 |
| 40 | dichloro | 6 | Zn (99) | 2 | ZnCl2 | 2 | DMA 60 | 100–110 | 24 | 100 | 49 |
| 41 | dichloro | 5.8 | Mn | 2 | None | | DMA 60 | 26–110 | 24 | 0 | 0 |
| 42 | dichloro | 5.6 | Cd | 2 | None | | DMA 60 | 100–110 | 48 | 73 | 6 |
| 43 | dichloro | 6.3 | Hg | 2 | None | | DMA 60 | 26–110 | 10 | 0 | 0 |
| 44 | dichloro | 5.8 | Ni | 2 | None | | DMA 60 | 26–100 | 10 | 0 | 0 |
| 45 | dichloro | 400 | Zn | 2 | None | | DMA 4000 | 100–110 | 24 | 85 | 39 |
| 46 | dichloro | 720 | Zn | 2 | None | | DMA 7200 | 105 | 20 | 100 | 59 |
| 47 | dichloro | 1200 | Zn | 2 | None | | DMA 12000 | 100–105 | 48 | 99 | 53 |
| 48 | dichloro | 50.4 | Zn | 2 | None | | DMA 500 | 97–101 | 22 | 91 | 60 |
| 49 | dichloro | 51.2 | Zn | 2 | None | | DMA 500 | 98–101 | 22 | 47 | 66 |
| 50 | dichloro | 49.7 | Zn | 2 | None | | DMA 500 | 98–102 | 19 | 79 | 68 |

Having thus described certain embodiments of the present invention, various alterations, modifications and improvements will be apparent to those skilled in the art. Such alterations, modifications and improvements are intended to be within the spirit and scope of the invention. The materials used as well as their relative quantities maybe any required. Furthermore, mixtures of reagents and solvents may be effective in producing AF4. Accordingly, the foregoing description is by way of example only and is not intended as limiting. The invention is limited only as defined in the following claims and the equivalents thereto.

What is claimed is:

1. A method of making parylene AF4, the method comprising the steps of:
   mixing a dihalo compound with a reducing agent comprising zinc or magnesium to form a reaction mixture, the dihalo compound comprising at least about $1 \times 10^{-3}$ weight percent of the reaction mixture; and
   reacting the reaction mixture to form product materials including the parylene AF4.

2. The method according to claim 1, wherein the mixing step includes mixing a transition metal catalyst such that the transition metal catalyst comprises at least about $1 \times 10^{-3}$ weight percent of the reaction mixture.

3. The method according to claim 2, wherein the mixing step includes mixing a solvent.

4. The method according to claim 3, wherein the reacting step includes producing the parylene AF4 in a yield of at least about 20 molar percent based on the dihalo compound used in the mixing step.

5. The method according to claim 1, wherein the reacting step includes producing the parylene AF4 in a yield of at least about 20 molar percent based on the dihalo compound used in the mixing step.

6. The method according to claim 1, wherein the mixing step includes mixing a solvent.

7. The method according to claim 1, wherein the reacting step includes forming less than about 10 molar percent of linear byproduct based on the product materials formed.

8. The method according to claim 1, wherein the reacting step includes forming less than about 10 molar percent reduction byproduct based on the product materials formed.

9. The method according to claim 1, wherein the mixing step includes mixing a reducing agent having an electrochemical potential of from about +0.45 volts to about +2.5 volts relative to a standard hydrogen potential.

10. The method according to claim 1, wherein the mixing step includes mixing a reducing agent comprising a zinc powder or a magnesium powder.

11. The method according to claim 1, wherein the mixing step includes mixing a reducing agent comprising a zinc powder.

12. A method of making parylene AF4, the method comprising the steps of:

mixing a dihalo compound with a reducing agent comprising zinc or magnesium to form a reaction mixture, the reducing agent comprising at least about $1 \times 10^{-3}$ weight percent of the reaction mixture; and reacting the reaction mixture to form product materials including the parylene AF4.

13. The method according to claim 12, wherein the mixing step includes mixing a solvent.

14. The method according to claim 13, wherein the reacting step includes producing the parylene AF4 in a yield of at least about 20 molar percent based on the dihalo compound used in the mixing step.

15. The method according to claim 12, wherein the reacting step includes producing the parylene AF4 in a yield of at least about 20 molar percent based on the dihalo compound used in the mixing step.

16. The method according to claim 12, wherein the mixing step includes mixing a solvent.

17. The method according to claim 12, wherein the reacting step includes forming less than about 10 molar percent of linear byproduct based on the product materials formed.

18. The method according to claim 12, wherein the reacting step includes forming less than about 10 molar percent reduction byproduct based on the product materials formed.

19. The method according to claim 12, wherein the mixing step includes mixing a reducing agent having an electrochemical potential of from about +0.45 volts to about +2.5 volts relative to a standard hydrogen potential.

20. The method according to claim 12, wherein the mixing step includes mixing a reducing agent comprising a zinc powder or a magnesium powder.

21. The method according to claim 12, wherein the mixing step includes mixing a reducing agent comprising a zinc powder.

22. A method of making parylene AF4, the method comprising the steps of:

mixing a dihalo compound with a reducing agent to form a reaction mixture, the reducing agent having an electrochemical potential of from about +0.45 volts to about +2.5 volts relative to a standard hydrogen potential; and reacting the reaction mixture to form product materials including the parylene AF4.

23. The method according to claim 22, wherein the mixing step includes mixing a solvent.

24. The method according to claim 22, wherein the reacting step includes producing parylene AF4 in a yield of at least about 20 molar percent based on the dihalo compound used in the mixing step.

25. The method according to claim 22, wherein the reacting step includes forming less than about 10 molar percent of linear byproduct based on the product materials formed.

26. The method according to claim 22, wherein the reacting step includes forming less than about 10 molar percent of reduction byproduct based on the product materials formed.

27. A method of making parylene AF4, the method comprising the steps of:

mixing a dihalo compound with a reducing agent comprising a zinc powder or a magnesium powder to form a reaction mixture, the dihalo compound comprising at least about $1 \times 10^{-3}$ weight percent of the reaction mixture; and reacting the reaction mixture to form product materials including the parylene AF4.

28. A method of making parylene AF4, the method comprising the steps of:

mixing a dihalo compound with a reducing agent comprising a zinc powder to form a reaction mixture, the dihalo compound comprising at least about $1 \times 10^{-3}$ weight percent of the reaction mixture; and reacting the reaction mixture to form product materials including the parylene AF4.

29. A method of making parylene AF4, the method comprising the steps of:

mixing a dihalo compound with a reducing agent comprising a zinc powder or a magnesium powder to form a reaction mixture, the reducing agent comprising at least about $1 \times 10^{-3}$ weight percent of the reaction mixture; and reacting the reaction mixture to form product materials including the parylene AF4.

30. A method of making parylene AF4, the method comprising the steps of:

mixing a dihalo compound with a reducing agent comprising a zinc powder to form a reaction mixture, the reducing agent comprising at least about $1 \times 10^{-3}$ weight percent of the reaction mixture; and reacting the reaction mixture to form product materials including the parylene AF4.

31. A method of making parylene AF4, the method comprising the steps of:

mixing a dihalo compound comprising 1,4-bis(chlorodifluoromethyl) benzene, 1,4-bis(bromodifluoromethyl) benzene, or 1,4-bis(iododifluoromethyl) benzene, with a reducing agent comprising zinc or magnesium to form a reaction mixture, the dihalo compound comprising at least about $1 \times 10^{-3}$ weight percent of the reaction mixture; and reacting the reaction mixture to form product materials including the parylene AF4.

32. The method according to claim 31 wherein the reducing agent comprises a zinc powder or a magnesium powder.

33. A method of making parylene AF4, the method comprising the steps of:

mixing a dihalo compound comprising 1,4-bis(chlorodifluoromethyl) benzene, 1,4-bis(bromodifluoromethyl) benzene, or 1,4-bis(iododifluoromethyl) benzene, with a reducing agent comprising zinc to form a reaction mixture, the dihalo compound comprising at least about $1 \times 10^{-3}$ weight percent of the reaction mixture; and reacting the reaction mixture to form product materials including the parylene AF4.

34. The method according to claim 33 wherein the reducing agent comprises a zinc powder.

35. A method of making parylene AF4, the method comprising the steps of:

mixing a dihalo compound comprising 1,4-bis(chlorodifluoromethyl) benzene, 1,4-bis(bromodifluoromethyl) benzene, or 1,4-bis(iododifluoromethyl) benzene, with a reducing agent comprising zinc or magnesium to form a reaction mixture, the reducing agent comprising at least about $1 \times 10^{-3}$ weight percent of the reaction mixture; and reacting the reaction mixture to form product materials including the parylene AF4.

36. The method according to claim 35 wherein the reducing agent comprises a zinc powder or a magnesium powder.

37. A method of making parylene AF4, the method comprising the steps of:

mixing a dihalo compound comprising 1,4-bis(chlorodifluoromethyl) benzene, 1,4-bis(bromodifluoromethyl) benzene, or 1,4-bis(iododifluoromethyl) benzene, with a reducing agent comprising zinc to form a reaction mixture, the reducing agent comprising at least about $1\times10^{-3}$ weight percent of the reaction mixture; and reacting the reaction mixture to form product materials including the parylene AF4.

38. The method according to claim 37 wherein the reducing agent comprises a zinc powder.

39. A method of making parylene AF4, the method comprising the steps of:

mixing a dihalo compound comprising 1,4-bis(chlorodifluoromethyl) benzene with a reducing agent comprising zinc to form a reaction mixture, the dihalo compound comprising at least about $1\times10^{-3}$ weight percent of the reaction mixture; and reacting the reaction mixture to form product materials including the parylene AF4.

40. The method according to claim 39 wherein the reducing agent comprises a zinc powder.

41. A method of making parylene AF4, the method comprising the steps of:

mixing a dihalo compound comprising 1,4-bis(chlorodifluoromethyl) benzene with a reducing agent comprising zinc to form a reaction mixture, the reducing agent comprising at least about $1\times10^{-3}$ weight percent of the reaction mixture; and reacting the reaction mixture to form product materials including the parylene AF4.

42. The method according to claim 40 wherein the reducing agent comprises a zinc powder.

\* \* \* \* \*